United States Patent [19]

Tolman et al.

[11] Patent Number: 5,110,799
[45] Date of Patent: May 5, 1992

[54] ANTIHERPETIC AGENTS

[75] Inventors: Richard L. Tolman, Warren; Wallace T. Ashton; Mu T. Wu, both of Clark, all of N.J.

[73] Assignee: Merck & Co., Inc., Rahway, N.J.

[21] Appl. No.: 386,071

[22] Filed: Jul. 28, 1989

[51] Int. Cl.$^5$ .................. A61K 37/00; C07D 233/64
[52] U.S. Cl. ........................................ 514/19; 548/344
[58] Field of Search ........................... 514/19; 548/344

[56] References Cited

U.S. PATENT DOCUMENTS

| | | | |
|---|---|---|---|
| 4,374,829 | 2/1983 | Harris, Jr. et al. | 424/177 |
| 3,632,753 | 1/1972 | Elton et al. | 514/19 |
| 3,790,438 | 6/1973 | Cook et al. | 514/19 |
| 4,752,602 | 6/1988 | Apsky et al. | 514/19 |
| 4,795,740 | 1/1989 | Cohen et al. | |
| 4,814,432 | 3/1989 | Freidinger et al. | 530/329 |
| 4,863,904 | 9/1989 | Iizuka | 548/344 |

FOREIGN PATENT DOCUMENTS

| | | | |
|---|---|---|---|
| 0049506 | 4/1982 | European Pat. Off. | |
| 0079522 | 5/1983 | European Pat. Off. | |
| 0128762 | 12/1984 | European Pat. Off. | 548/344 |
| 246630A2I1 | 5/1987 | European Pat. Off. | |
| 2185024A | 12/1986 | United Kingdom | |

OTHER PUBLICATIONS

E. Nicholaides, et al., *Potential Antiviral Agents, J. Med. Chem., II,* 74 (1968).
E. A. Cohen et al., Nature, 321: 441-443 (1986) III.
B. M. Dutia et al., Nature, 321: 439-441 (1986).
P. Gaudreau et al., J. of Biological Chem., 262: 12413-12416 (1987).
Blumenstein et al., "Synthetic Non-peptide Inhibitors of HIV Protease," Biochem. Biophys. Res. Comm., 163, No. 2 (1989) pp. 980-987.
Denkewalter et al., "Progress in Dry Research", vol. 10 (1966) p. 510-512.
Bryer, Medicinal Chem. 2nd ed. Jun. 27, 1960, Interscience Publishers Inc., p. 565-601.
Plattner et al., J. Med., Chem. 1988, 31, pp. 2277-2288 Renin Inhibitor, Dipeptide Analogues of a Protein.

*Primary Examiner*—Lester L. Lee
*Assistant Examiner*—E. J. Kraus
*Attorney, Agent, or Firm*—Hesna J. Pfeiffer; Raymond M. Speer; Gerard H. Bencen

[57] ABSTRACT

A series of carboxyl-containing N-alkyldipeptides have been found to posess antiviral potency—specifically against herpes simplex virus—by selectively inhibiting the viral ribonucleotide reductase enzyme.

4 Claims, No Drawings

ANTIHERPETIC AGENTS

BACKGROUND OF THE INVENTION

Herpes simplex viruses (HSV) cause a wide spectrum of diseases ranging from mild to severe mucosal lesions, keratitis, and encephalitis. Both HSV types 1 and 2 are widely distributed in the western adult population, with reported exposure rates to HSV-1 estimated to be as high as 90%. The recent and rapid increase in the number of genital HSV infections is reflected by serology studies which indicate that 15-35% of the North American adult population have been exposed to HSV 2.

The major effort to develop antiherpetic drugs has historically centered on nucleoside analog inhibitors of HSV DNA polymerase. All currently used therapies are nucleoside analogs, acyclovir being the prime example. Oral or IV acyclovir is the therapy of choice for most infections. Topical acyclovir, vidarabine or idoxuridine are all used for herpes keratitis, the leading cause of corneal blindness in this country. However, considering the complex replication cycle and large number of virally encoded proteins, other potential targets for antiviral drugs must exist. HSV ribonucleotide reductase (RR) is one such target; the viral-specified enzyme is markedly different from mammalian counterparts. HSV-RR catalyzes the reduction of the four ribonucleotides to the corresponding deoxyribonucleotides required for DNA replication. Published analysis of viral RR mutants indicated that the enzyme is not essential for growth of herpes in culture (Goldstein and Weller, Virology 166: 41 (1988)), but is essential in vivo (Spector, *Pharmaceutical Therapy*, 31, 295 (1985)). Herpes RR inhibitors have been shown to possess antiherpetic activity per se (Shipman et al., *Antiviral Research*, 6: 197 (1986)) and also to potentiate or synergize the action of acyclonucleoside antiviral agents (Spector et al., *Proc. of the Nat. Acad. Of Sci.*, 86: (1989)).

Dutia et al., Nature 321: 439-441 (1986) and Cohen et al., Nature 321: 441-443 (1986) and U.S. Pat. No. 4,795,740, both disclosed that the nonapeptide Tyr Ala Gly Ala Val Val Asn Asp Leu, inhibited in vitro the activity of this enzyme. In addition Dutia et al., op. cit., also disclosed that its 8-desalanine homolog, Tyr gly Ala Val Val Asn Asp Leu, also inhibited in vitro the activity of this enzyme. Gaudreau et al., J. Biol. Chemistry, 262 12413 (1987) disclosed structure activity studies of analogs of the nonapeptide described above.

OBJECT OF THE INVENTION

It is the object of the present invention to describe novel dipeptides which inhibit the activity of the ribonucleotide reductase enzyme of viruses, particularly the herpes simplex virus. Another object is to describe inhibitor peptides that lack or show weak inhibitory activity for mammalian ribonucleotide reductases.

SUMMARY OF INVENTION

A series of carboxyl-containing N-alkyl dipeptides have been found to inhibit the activity of the ribonucleotide reductase enzyme of herpes simplex virus in vitro.

The present invention provides novel dipeptide compounds of the formula:

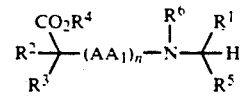

wherein:
AA$_1$ is histidine, aspartic acid or any of the enantiomorphic forms thereof;
R$_1$ is:
a) hydrogen;
b) C$_2$-C$_6$ alkenyl;
c) C$_2$-C$_6$ alkynyl;
d) C$_3$-C$_7$ cycloalkyl;
e) C$_5$-C$_7$ cycloalkenyl;
f) phenyl;
g) monocyclic heteroaromatic ring system;
h) aromatic or heteroaromatic polycyclic ring system;
i) C$_1$-C$_6$ alkyl:
j) a group f)-i) above monosubstituted by: OH, OMe, NH$_2$, SMe, C$_{1-4}$ alkyl, CO$_2$H, or CN;
k) C$_1$-C$_4$ alkyl monosubstituted by b)-j) above;
R$^2$ and R$^3$ are independently:
l) C$_2$-C$_6$ alkenyl;
m) C$_2$-C$_6$ alkynyl;
n) C$_3$-C$_7$ cycloalkyl;
o) C$_5$-C$_7$ cycloalkenyl;
p) phenyl;
q) monocyclic heteroaromatic ring system;
r) heteroaromatic polycyclic ring system;
s) C$_1$-C$_6$ alkyl;
t) a group p)-s) above monosubstituted by: OH, OMe, NH$_2$, SMe, C$_{1-4}$ alkyl, CO$_2$H, or CN;
u) C$_1$-C$_4$ alkyl monosubstituted by l)-t) above;
v) hydrogen;
w) R$^2$ and R$^3$ combined to form a C$_3$-C$_5$ diradical;
R$^4$ is: H, C$_3$-C$_7$ cycloalkyl, C$_1$-C$_6$ alkyl or C$_1$-C$_4$ alkyl substituted by one of these substituents;
R$^5$ is: —CO$_2$R$^4$, —PO$_3$R$^4$, CH$_2$CO$_2$R$^4$, CONHCH$_2$CO$_2$H, or —CONH$_2$;
R$^6$ is: H, CH$_3$ or R$^1$ and R6 are combined to form a C$_2$-C$_4$ alkyl diradical;
n is 1 or 0; and the pharmaceutically acceptable salts thereof.

The terms "alkyl, alkenyl and alkynyl" are intended to include linear and branched structures.

The term "alkyl" is intended to include methyl, ethyl, propyl, isopropyl, butyl, sec- and tert-butyl, pentyl, hexyl and the like.

The term "alkenyl" is intended to include vinyl, allyl, isopropenyl, pentenyl, hexenyl and the like.

The term "alkynyl" is intended to include acetylene, propylene, butylene and the like.

The term "cycloalkyl" is intended to include cyclopropyl, cyclobutyl, cyclopentyl, cyclohexyl, cycloheptyl and the like.

The term "cycloalkenyl" is intended to include cyclopentenyl, cyclohexenyl, cycloheptenyl and the like.

The term "heteroaromatic polycyclic ring system" is intended to include quinoline, isoquinoline, indole, benzofuran, benzothiophene and the like.

The term "aromatic polycyclic ring system" is intended to include napthalene, phenanthrene and the like.

The term "monocyclic heteroaromatic ring system" is intended to include pyridine, thiophene, thiazole, furan, imidazole, pyrimidine and the like.

Some of the compounds described herein contain one or more centers of asymmetry and may thus give rise to diastereoisomers and optical isomers.

The present invention is meant to comprehend such possible diastereomers as well as their racemic and resolved optically active forms.

Some of the compounds described herein contain olefinic double bonds and unless specified otherwise, are meant to include both E and Z geometric isomers.

Preferably $AA_1$ is histidine or the enantiomorphic form thereof.

Preferably $R^1$ is selected from the group: H, $CH_3$, $CH_2CH(CH_3)_2$.

Preferably $R^2$ and $R^3$ are independently
a) hydrogen;
b) phenyl;
c) monocyclic heteroaromatic ring system;
d) heteroaromatic polyclyclic ring system;
e) $C_1-C_6$ alkyl;
f) a group b)-e) above monosubstituted by: OH, OMe, $NH_2$, SMe, $C_{1-4}$ alkyl, $CO_2H$, or CN;
g) $C_1-C_4$ alkyl monosubstituted by b)-f) above.

Preferably $R^4$ is H.

Preferably $R^5$ is $CO_2R^4$ or $PO_3R^4$.

Preferably $R^6$ is H or $R^6$ and $R^1$ are combined to form a $C_2-C_4$ alkyl diradical.

When $R^1$ is hydrogen, $C_1-C_6$ alkyl or substituted or unsubstituted phenyl $C_1-C_4$ alkyl, the most preferred $R^2$ is substituted or unsubstituted phenyl $C_1-C_4$ alkyl or hydrogen.

One aspect of this invention involves a pharmaceutical composition comprising an antiherpes virally effective amount of a compound of Formula I, or a therapeutically acceptable salt thereof, and a pharmaceutically or veterinarily acceptable carrier.

Another aspect of this invention involves a method of treating herpes viral infection in a mammal by administering, either topically, parenterally or systemically, to the mammal an antiherpes virally effective amount of the peptide of Formula I, or a therapeutically acceptable salt thereof as defined hereinafter.

Another aspect of this invention involves a method of treating viral infections in mammals comprising administering to the mammal an antivirally effective amount of the peptide of Formula I with another antiviral agent whose mechanism of action involves specifically an enzyme of nucleic acid metabolism, such as an acyclonucleoside or related compounds. Potent synergy has been demonstrated for such combination Processes for preparing the peptides of Formula I are described hereinafter.

DETAILED DESCRIPTION OF THE INVENTION

It has now been found that a series of carboxyl-containing N-alkyl and substituted alkyl dipeptides inhibit the activity of the ribonucleotide reductase enzyme of herpes simplex virus in vitro. This inhibitory activity has been shown in vitro to be specific for the virus and does not affect mammalian reductase enzymes. This enzyme is required for replication of the herpes simplex virus.

The dipeptides of the present invention and the amides and salts thereof can be manufactured according to known synthetic methods, i.e., by condensing suitably activated amino acids. The N-alkyl side chain can then be attached to the dipeptide unit according to known synthetic methods, i.e., by condensing the dipeptide unit with a suitably substituted alkyl keto acid and subsequent reduction of the imine with sodium cyanoborohydride or by the reaction of the dipeptide unit with a suitably substituted a-halo carboxylic acid or ester in the presence of an organic base. Similarly, the N-substituent may be incorporated before the condensation between the two amino acids.

The condensation between two amino acids can be carried out according to the usual condensation methods such as azide method, mixed acid anhydride method, DCC (dicyclohexylcarbodiimide) method, active ester method (p-nitrophenyl ester method, N-hydroxysuccinimide ester method cyanomethyl ester method; etc.), Woodward reagent K method, carbonyl diimidazole method, oxidation reduction method or a method using any of the condensation-enhancing reagents (i.e. benzotriazol-1-yloxy-tris(dimethylamino) phosphonium hexafluorophosphate (BOP) or hydroxy benzotriazole (HOBT). These condensation reactions may be done in the liquid phase.

As is usual in peptide synthesis, it is necessary to protect/deprotect the a and 1-side chain as occasion demands. The applicable protective groups to amino groups are exemplified such as benzyloxycarbonyl (hereinafter abbreviated as Z), o-chlorobenzyloxycarbonyl [Z(2-Cl)], p-nitrobenzyloxycarbonyl [Z(NO2)], p-methoxybenzyloxycarbonyl [Z(OMe)], t-butoxycarbonyl (Boc), t-amyloxycarbonyl (Acc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthalyl, formyl, 2-nitrophenylsulfenyl (NPS), diphenylphosphinothioyl (Ppt), dimethylphosphinothioyl (Mpt) and the like.

As protective groups for carboxy group there can be exemplified, for example, benzyl ester (OBzl), 4-nitrobenzyl ester [OBzl(NO2)], t-butyl ester (OBut), 4-pyridylmethyl ester (Opic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1,3,5,-trimethylphenylsulfonyl (Mts), and the like. The thiol group in cysteine may be protected with benzyl, p-methoxybenzyl, triphenylmethyl, acetylaminomethyl, ethylcarbamoyl, 4-methylbenzyl, 2,4,6-trimethylbenzyl (Tmb) etc., and the hydroxyl group in serine can be protected with benzyl, t-butyl, acetyl, tetrahydropyranyl etc.

Conventional methods of peptide synthesis as described, for example, by Schroder et al., "The Peptides", Vol. I Academic Press, 1965, or Bodanszky et al., "Peptide Synthesis", Interscience Publishers, 1966 or McOmie (ed.), "Protective Groups in Organic Chemistry", Plenum Press, 1973 or "The Peptides: Analysis Synthesis, Biology", 2 Chapter 1, by Barany et al., Academic Press, 1980, the disclosures of which are hereby incorporated by reference.

The compounds of the instant invention are novel valuable antiherpetic agents. Since the mode of pharmacological action of the compounds of the present invention differs from previously known antiherpetic agents the safety liabilities associated with previous antiherpetic agents may not be manifested.

Therapeutically-acceptable salts are prepared by recrystallization of the desired cytosine, uracil, or thymine derivative as the free base or as the acetate or hydrochloride from the aqueous dilute acid of choice. Alkali metal salts of thymine and uracil derivatives may be made by standard techniques, for example, by dissolving such derivatives in water containing one equivalent of an alkali metal hydroxide, followed by evaporation to dryness.

Additionally, the compounds of the instant invention may be used therapeutically in combination with antiviral acyclonucleosides such as acyclovir or ganciclovir. The compounds of the instant invention are known to be potent synergists of such antiviral agents.

In an aspect of the invention there is provided a pharmaceutical composition or preparation comprising a compound of the Formula I as hereinbefore defined; or a therapeutically acceptable salt thereof, together with a pharmaceutically acceptable carrier therefore. In a particular aspect the pharmaceutical composition comprises a compound of the present invention in effective unit dosage form.

As used herein the term "effective unit dosage" or "effective unit dose" is denoted to mean a predetermined antiviral amount sufficient to be effective against the viral organisms in vivo. Pharmaceutically-acceptable carriers are materials useful for the purpose of administering the medicament, and may be solid, liquid, or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops, etc., depending on whether the preparation is used to treat internal or external viral infections.

For internal infections the compositions are administered orally or parenterally at dose levels of about 0.1 to 250 mg per kg, preferably 1.0 to 50 mg per kg of mammal body weight, and are used in man in a unit dosage form, administered, e.g. a few times daily, in the amount of 1 to 250 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening, or emulsifying agents may be included. Tablets and granules are preferred, and these may be coated.

For parenteral administration or for administration as drops, as for eye infections, the compounds may be presented in aqueous solution in a concentration of from about 0.1 to 10%, more preferably 0.1 to 7%, most preferably 0.2% w/v. The solution may contain antioxidants, buffers, etc.

Alternatively, for infections of the eye, or other external tissues, e.g. mouth and skin, the compositions are preferably applied to the infected part of the body of the patient as a topical ointment or cream. The compound may be presented in an ointment, for instance, with a water soluble ointment base, or in a cream, for instance with an oil in a water cream base, in a concentration of from about 0.1 to 10%, preferably 0.1 to 7%, most preferably 1% w/v.

The following examples illustrate the present invention without, however, limiting the same thereto. All temperatures are expressed in degrees Celsius.

EXAMPLE 1

($N^\alpha$-Carboxymethyl-L-histidyl)-L-leucine

Step A: ($N^\alpha$-t-Butoxycarbonyl-$N^{im}$-2,4-dinitrophenyl-L histidyl)-L-leucine benzyl ester A mixture of 1.32 g of $N^\alpha$-t-butoxycarbonyl-$N^{im}$-2,4-dinitrophenyl-L-histidine, 663 mg of L-leucine benzyl ester, 639 mg of N,N'-dicyclohexyl carbodiimide, and 944 mg of 1-hydroxybenzotriazole in 10 ml of anhydrous $CH_2Cl_2$ was stirred for 41 hours at ambient temperature. The reaction mixture was then filtered and the filtrate was concentrated under vacuum. The concentration residue was dissolved in $Et_2O$ and the mixture again filtered and concentrated under vacuum to give an orange gum.

Chromatography over silica gel (97 methylene chloride: 3 methanol) provided 1.06 g of the title compound as a stiff yellow foam.

Step B:
($N^\alpha$-Carboxymethyl-$N^{im}$-2,4-dinitrophenyl-L-histidyl)-L-leucine dibenzyl ester The dipeptide (1.00 g) (Step A) was dissolved in 4 ml of anhydrous trifluoroacetic acid and the reaction mixture was stirred at ambient temperature under an inert atmosphere for 2 hours. The reaction solution was then evaporated under a stream of nitrogen and the residue dissolved in ethanol. The ethanolic solution was evaporated under a stream of nitrogen and the residue dissolved in ethyl acetate. The solution was washed twice with saturated aqueous sodium carbonate solution. The organic phase was dried with sodium sulfate, filtered and concentrated under vacuum to give 840 mg of a brownish foam.

This foam was dissolved in 5 ml of anhydrous tetrahydrofuran and 223 ml of triethylamine was added to the solution. A solution of 301 ml of benzyl bromoacetate in 2 ml of anhydrous tetrahydrofuran was added dropwise to the stirring solution. After the addition was complete, the reaction flask was stoppered and the reaction stirred at ambient temperature for 16 hours. The reaction was now a slurry. Triethylamine (55.6 ml) was added and the reaction mixture stirred at ambient temperature for 24 hours. The mixture was then diluted with ethyl acetate and filtered. The solid was rinsed with ethyl acetate and the filtrate and rinses combined and concentrated under vacuum. The dark red-orange residue was dissolved in ethyl acetate and the solution washed twice with 20 ml of saturated aqueous ammonium chloride solution. The organic phase was then washed with saturated aqueous sodium carbonate solution and then dried with sodium sulfate, filtered and the filtrate concentrated under vacuum to give 1.28 g of a dark red-orange oil.

Chromatography on silica gel (gradient 0%-6% v/v i-propyl alcohol in methylene chloride) provided 660 mg of the title compound as an orange glass.

Step C: (N$^\alpha$-Carboxymethyl-L-histidyl)-L-leucine dibenzyl ester

Thiophenol (102.5 ml) was added to a solution of 606 mg of the dibenzyl ester (Step B) in 4 ml of methylene chloride. The reaction solution was stirred at ambient temperature for 6 hours and then diluted with 30 ml of ethyl ether. The solution was washed three times with 20 ml of saturated aqueous sodium carbonate solution. The organic phase was dried over sodium sulfate, filtered and concentrated under vacuum to give an orange semisolid.

Chromatography over silica gel (gradient 97 methylene chloride:3 methanol:0.3 concentrated ammonium hydroxide to 95:5:0.5 of same provided 353 mg of the title compound as a golden gum.

Step D: (N$^\alpha$-Carboxymethyl-L-histidyl)-L-leucine

A solution of 304 mg of the dibenzyl ester (Step C) in 10 ml of glacial acetic acid was added to a suspension of 50 mg of 10% palladium on carbon in 5 ml of distilled water. The mixture was shaken under a 36.2 psig hydrogen atmosphere for 1.5 hours. The mixture was filtered through Celite and the filter rinsed with distilled water. The filtrate and rinse were combined and concentrated under vacuum to a yellow gum. The gum was treated with hot acetone and the resulting solid collected, washed with acetone and dried under vacuum at 50% to provide 189 mg of the title compound as a yellow powder.

p.m.r. (DMSO-d$_6$) δ:0.83 (d, 3 H), 0.87 (d, 3 H), 1.3–1.65 (m, 3 H), 2.72 (dd, 1 H), 2.86 (dd, 1 H), 3.10 (d, 1 H), 3.28 (d, 1 H), 3.39 (m, 1 H), 4.23 (m, 1 H), 6.89 (s, 1 H), 7.63 (s, 1 H), 8.16 ppm (d, 1 H); M.S.(FAB): m/e 327 (M+H)$^-$.

EXAMPLE 2

(N$^\alpha$-Carboxymethyl-D-histidyl)-L-leucine

Using the procedures of Example 1(Steps A-D) but substituting N$^\alpha$-t-butoxycarbonyl-N$^{im}$-2,4-dinitrophenyl-D-histidine for the bis-protected L-histidine in Example 1 (Step A) provided the title compound as a pale yellow powder.

p.m.r. (DMSO-d$_6$) δ:0.79 (d, 3 H), 0.85 (d, 3 H), 1.4–1.6 (m, 3 H), 2.72 (dd, 1 H), 2.84 (dd, 1 H), 3.13 (d, 1 H), 3.23 (d, 1 H), 3.44 (t, 1 H), 4.17 (m, 1 H), 6.85 (s, 1 H), 7.60 (s, 1 H), 8.21 ppm (d, 1 H); M.S. (FAB): m/e 327 (M+H)$^+$.

EXAMPLE 3

(N$^\alpha$-Carboxymethyl-L-histidyl)-D-leucine

Step A: (N$^\alpha$-t-Butoxycarbonyl-N$^{im}$-2,4-dinitrophenyl-L-histidyl)-D-leucine benzyl ester D-Leucine benzyl ester p-toluene sulfonate (1.18 g) was partitioned between 30 ml of diethyl ether and 15 ml of saturated aqueous sodium carbonate solution. The organic phase was dried with sodium sulfate, filtered and concentrated under vacuum to provide 620 mg of D-leucine benzyl ester as a colorless oil.

The D-leucine benzyl ester (620 mg) was dissolved in 10 ml of anhydrous methylene chloride and 1.23 g of N$^\alpha$-t-butoxycarbonyl-N$^{im}$-2,4-dinitrophenyl-L-histidine, 1.24 g of benzotriazol-1-yloxytris(dimethylamino)phosphonium hexafluorophosphate ("BOP reagent") and 390 ml of triethylamine were added. The reaction solution was stirred 40 hours at ambient temperature, then the solution was concentrated under vacuum. The residual oil was dissolved in 50 ml of ethyl acetate and the solution washed twice with 25 ml of saturated aqueous ammonium chloride solution. The organic phase was washed twice with 30 ml of saturated aqueous sodium bicarbonate solution, then dried with magnesium sulfate, filtered and concentrated under vacuum to provide an orange gum.

Chromatography over silica gel (gradient 98 methylene chloride:2 isopropyl alcohol to 97:3 of the same) provided 1.29 g of the title compound as a stiff yellow foam.

Step B: (N$^\alpha$-Carboxymethyl-N$^{im}$-2,4-dinitrophenyl-L-histidyl)-L-leucine dibenzyl ester Using the procedure of Example 1 (Step B) but substituting the title compound of Example 3 (Step A) for the dipeptide of Example 1 (Step A) there was obtained 359 mg of the title compound.

Step C: (N$^\alpha$-Carboxymethyl-L-histidyl)-D-leucine dibenzyl ester

Using the procedure of Example 1 (Step C) but substituting the title compound of Example 3 (Step B) for the dipeptide of Example 1 (Step B) there was obtained 175 mg of the title compound.

Step D: (N$^\alpha$-Carboxymethyl-L-histidyl)-D-leucine

Using the procedure of Example 1 (Step D) but substituting the title compound of Example 3 (Step C) for the dibenzyl ester of Example 1 (Step C) there was obtained 92 mg of the title compound as an off-white powder.

p.m.r. (DMSO-d$_6$) δ:0.79 (d, 3 H), 0.85 (d, 3 H), 1.4–1.6 (m, 3 H), 2.72 (dd, 1 H), 2.84 (dd, 1 H), 3.12 (d, 1 H), 3.22 (d, 1 H), 3.44 (t, 1 H), 4.16 (m, 1 H), 6.85 (s, 1 H), 7.60 (s, 1 H), 8.23 ppm (d, 1 H); M.S. (FAB): m/e 327 (M+H)$^+$.

EXAMPLE 4

(N$^\alpha$-Carboxymethyl-L-histidyl)glycine

Step A: (N$^\alpha$-t-Butoxycarbonyl-N$^{im}$-2,4 dinitrophenyl-L-histidyl)glycine benzyl ester Glycine benzyl ester hydrochloride (605 mg) was partitioned between 15 ml of saturated aqueous sodium carbonate solution and 30 ml of diethyl ether. The organic phase was dried over sodium sulfate, filtered and concentrated under vacuum to provide 507 mg of a clear oil.

The oil above was dissolved in 10 ml of methylene chloride and 1.32 g of N$^\alpha$-t-butoxycarbonyl-N$^{im}$-2,4-dinitrophenyl-L-histidine, 618 mg of N,N'-dicyclohexylcarbodiimide and 918 mg of 1-hydroxybenzotriazole were added. The reaction mixture was stirred at ambient temperature for 4 days. The reaction mixture was then filtered and the filtrate concentrated under vacuum. The residue was dissolved in 30 ml of ethyl acetate, filtered, then washed twice with 20 ml of saturated aqueous sodium bicarbonate. The organic phase was washed 2 times with saturated aqueous ammonium chloride solution, then dried with magnesium sulfate. The mixture was filtered and concentrated under vacuum to provide a yellow foam.

Chromatography over silica gel (gradient 99 methylene chloride:1 isopropyl alcohol to 95:5 same) provided 1.12 g of the title compound as an oily residue.

Step B: (N$^\alpha$-Carboxymethyl-N$^{im}$-2,4-dinitrophenyl-L-histidyl)glycine dibenzyl ester The glycine benzyl ester (Step A) (700 mg) was dissolved in 2 ml of methylene chloride and 2 ml of anhydrous trifluoroacetic acid. The solution was stirred at ambient temperature for 2 hours under nitrogen atmosphere. The solution was then evaporated to dryness under a nitrogen stream. The residue was dissolved in 40 ml of ethyl acetate and this solution washed twice with 30 ml of saturated sodium carbonate solution. The organic phase was dried with sodium sulfate, filtered and concentrated under vacuum to a brown foam.

The crude residue above was dissolved in 5 ml of anhydrous tetrahydrofuran and 171 ml of distilled triethylamine was added. Benzyl 2-bromoacetate (232 ml) was added and the reaction solution was stirred under a nitrogen atmosphere for 24 hours. The mixture was then concentrated under vacuum and the residue taken up in 40 ml of ethyl acetate. The mixture was filtered and the solid rinsed with ethyl acetate. The filtrate and rinse were combined and washed twice with 20 ml of saturated aqueous ammonium chloride, then with 20 ml of saturated aqueous sodium carbonate solution. The organic phase was dried with magnesium sulfate, filtered and concentrated under vacuum to provide a brown gum.

Chromatography over silica gel (97 methylene chloride:3 isopropanol) provided 250 mg of the title compound as a glass.

Step C: (N$^\alpha$-Carboxymethyl-L-histidyl)glycine dibenzyl ester

To a solution of 240 mg of the glycine diester (Step B) in 2.5 ml of methylene chloride was added 45 ml of thiophenol and the solution stirred in a stoppered flask at ambient temperature for 24 hours. The reaction mixture was diluted with 25 ml of ethyl ether and the solution washed three times with 15 ml of saturated aqueous sodium carbonate solution. The organic phase was dried with magnesium sulfate, filtered and concentrated under vacuum to give 261 mg of a yellow oil.

Chromatography over silica gel (90 methylene chloride:10 methanol:1 concentrated aqueous ammonium hydroxide) provided 89 mg of the title compounds as a gum.

Step D: (N$^\alpha$-Carboxymethyl-L-histidyl)glycine

A solution of 85 mg of the glycine dibenzyl ester (Step C) in 4 ml of glacial acetic acid was added to a suspension of 18 mg of 10% palladium on carbon in 2 ml water. The mixture was shaken under a 41 psi hydrogen atmosphere for 1.5 hours at ambient temperature, then filtered through Celite. The filter was rinsed with water and the filtrate and rinse combined and concentrated under vacuum to a glass. The glass was treated with acetone and the solid which formed was collected and washed with acetone. The solid was dried at 60° C. under vacuum to provide 32 mg of the title compound.
p.m.r. (D$_2$O) δ:3.5–3.9 (m, 5H), 4.08 (d, 1 H), 4.46 (m, 1 H), 7.57 (s, 1 H), 8.74 ppm (s, 1 H); M.S. (FAB): m/e 293 (M+Na)$^+$.

EXAMPLE 5
(N$^\alpha$-Carboxymethyl-L-aspartyl)-L-leucine

Step A: (N$^\alpha$-t-Butoxycarbonyl-L-aspartyl)-L-leucine dibenzyl ester

L-leucine benzyl ester p-tosylate (1.30 g) was partitioned between 30 ml of saturated aqueous sodium carbonate and 50 ml of diethylether. The organic phase was dried with magnesium sulfate, filtered and concentrated under vacuum to provide an oil.

The residual oil was dissolved in 10 ml anhydrous methylene chloride and 1.26 g of N$^\alpha$-t-butoxycarbonyl-L-aspartic-β-benzyl-α-N-hydroxysuccinimide diester was added. The reaction solution was stirred at ambient temperature for 48 hours, then concentrated under vacuum to an oil. The residual oil was dissolved in 50 ml of ethyl acetate and the solution washed twice with saturated aqueous sodium bicarbonate solution. The organic phase was washed twice with saturated aqueous ammonium chloride solution, then dried with magnesium sulfate, filtered and concentrated under vacuum to provide a clear oil.

Chromatography over silica gel (99 chloroform:1 methanol) provided 1.49 g of the title compound as a clear oil.

Step B: (N$^\alpha$-Carboxymethyl-L-aspartyl)-L-leucine tribenzyl ester

Using the procedure of Example 1 (Step B) but substituting the benzyl ester of Example 5 (Step A) for the benzyl ester of Example 1 (Step A) there was obtained 1.04 g of the title compound as a yellow oil.

Step C: (N$^\alpha$-Carboxymethyl-L-aspartyl)-L-leucine

Using the procedure of Example 1 (Step D) but substituting the tribenzyl ester of Example 5 (Step B) for the dibenzyl ester of Example 1 (Step C) provided 70 mg of the title compound as a white solid.
p.m.r. (DMgO-d$_6$) δ:0.84 (d, 3 H), 0.89 (d, 3 H), 1.4–1.7 (m, 3 H), 2.39 (dd, 1 H), 2.53 (dd, 1 H), 3.17 (d, 1 H), 3.29 (d, 1 H), 3.48 (m, 1 H), 4.23 (m, 1 H), 8.26 ppm (d, 1 H); M.S. (FAB): m/e 305 (M+H)$^+$.

EXAMPLE 6
N-[1-D,L-Carboxy-3-(4-hydroxyphenyl)propyl]-L-histidyl-β-(2-thienyl)-L-alanine

Step A: (N$^\alpha$-t-Butoxycarbonyl-N$^{im}$-t-butoxycarbonyl-L-histidyl)-β-(2-thienyl)-L-alanine A solution of 453 mg of N$^\alpha$-t-butoxycarbonyl-N$^{im}$-t-butoxycarbonyl-L-histidine succinimidate in 4 ml of acetonitrile was added to a solution of 172 mg of β-(2-thienyl)-L-alanine and 168 mg of sodium bicarbonate in 4 ml of water at ambient temperature. The solution was stirred at ambient temperature for 18 hours, then concentrated under vacuum to approximately half of its volume. The solution was then cooled in an ice bath and made acidic by adding 2 N aqueous hydrochloric acid solution. The white solid which separated was collected, washed with water and dried under vacuum to provide 329 mg of the title compound.

Step B: L-Histidyl-β-(2-thienyl)-L-alanine

A solution of 250 mg of the bis-t-butoxycarbonyl dipeptide (Step A) in 2.5 ml of trifluoroacetic acid was stirred 24 hours at ambient temperature then concentrated under vacuum at 60° to provide the title compound as a clear oil.

Step C:
N-[1-D,L-Carboxy-3-(4-hydroxyphenyl)propyl]-L-histidyl-β-(2-thienyl)-L-alanine A solution of the dipeptide (step B) and 400 mg of 4-(4-hydroxyphenyl)-2-oxobutanoic acid in 3 ml of water and 1 ml of ethanol was basified to pH 7.9 by adding concentrated aqueous sodium hydroxide solution acid and 200 mg of sodium cyanoborohydride was added. The mixture was stirred at ambient temperature for 96 hours. Dowex 50w resin was added to the reaction and the mixture applied to a 10 ml Dowex 50 column. The column was eluted with $H_2O$ until the eluent was neutral, then with 100 ml of 5% v/v ethanol in water. The column was then eluted with 3% v/v pyridine in water and this eluent concentrated under vacuum at 60°. The residue was dissolved in water and the solution was freeze dried to provide 152 mg of the title compound.

p.m.r ($D_2O$) δ:1.26 (t, 1 H), 1.28 (t, 1 H), 1.92 (m, 2 H), 2.54 (m, 2 H), 3.21 (m, 4 H), 3.69 (m, 1 H), 4.44 (m, 1 H), 6.90 (d, 2 H), 6.98 (m, 3 H), 7.26 (d, 2 H), 8.20 (s, 1 H), 8.35 (s, 1 H), 8.40 ppm (s, 1 H); MS (FAB): m/e 489 $(M+H)^+$.

EXAMPLE 7

N-[1-D,L-Carboxy-3-(4-hydroxyphenyl)propyl]-L-histidyl-L-homophenylalanine

Using the procedures of Example 6 (steps A-C) but substituting L-homophenylalanine for the β-(2-thienyl)-L-alanine in Example 6 (step A) provided the title compound.

p.m.r.: ($D_2O$) δ:2.00 (m, 2 H), 2.68 (m, 2 H), 3.10 (m, 2 H), 3.72 (m, 1 H), 3.84 (m, 1 H), 4.12 (m, 1 H), 6.88 (d, 2 H), 7.22 (d, 2 H), 7.28 (s, 5H), 8.20 (s, 1 H), 8.24 ppm (s, 1 H); M.S. (FAB): m/e 495 $(M+H)^+$.

EXAMPLE 8

N-[1-D,L-Carboxy-3-(4-hydroxyphenyl)propyl]-β-(4-thiazolyl)-L-alanyl-glycine

Step A: [$N^\alpha$-t-Butoxycarbonyl-β-(4-thiazolyl) alanyl]-glycine t-butyl ester Dicyclohexyl carbodiimide (226 mg) was added to a solution of 273 mg of $N^\alpha$-t-butoxycarbonyl-β-(4-thiazolyl)-L-alanine and 132 mg of glycine t-butylester in 5 ml of ethyl acetate at 0° C. The reaction solution was stirred at 0° C. for 0.5 hour, then at ambient temperature for 18 hours. 4 drops of glacial acetic acid was then added to the reaction mixture and the mixture filtered. The filtrate was concentrated under vacuum to provide 426 mg of the title compound as an oil.

Step B: β-(4-Thiazolyl)-L-alanyl glycine

Using the procedure of Example 6 (step B) but substituting the dipeptide of Example 8 (step A) for the dipeptide of Example 6 (step A) provided the title compound.

Step C:
N-[1-D,L-Carboxy-3-(4-hydroxyphenyl)propyl]-β-(4-thiazolyl-L-alanyl-glycine Using the procedure of Example 6 (step C) but substituting the dipeptide of Example 8 (step B) for the dipeptide of Example 6 (step B) provided the title compound.
M.S.(FAB): m/e 408$(M+H)^+$, 430$(M+Na)^+$.

EXAMPLE 9

N-[1-D,L-Carboxy-3-(4-hydroxyphenyl)propyl]-L-histidyl-L-phenylalanine hemiammonium, hemisodium salt L-Histidyl-L-phenylalanine (150 mg) and 426 mg of 4-(4-hydroxyphenyl)-2-oxobutanoic acid were partially dissolved in 3 ml of water and 1 ml of acetonitrile. Concentrated aqueous sodium hydroxide solution was added to adjust the pH to 7.0 and 30 mg of sodium cyanoborohydride was added to the clear solution. The mixture was stirred at ambient temperature for 40 hours, then 5 ml of Dowex 50 resin ($H^+$ cycle) was added. The mixture was stirred for 2 hours then applied to a 10 ml Dowex 50 resin column. The column was washed with 35 ml of 3:1 water:acetonitrile followed by 50 ml of 75 water:25 acetonitrile:10 concentrated aqueous ammonium hydroxide solution. The second eluate was concentrated under vacuum to provide 236 mg of a white solid. This residue was dissolved in methanol and chromatography over LH-20 resin (methanol), followed by dilution with dilute aqueous ammonium hydroxide and freeze drying provided 206 mg of the title compound as a white solid.

p.m.r ($D_2O$) δ:1.70 (m, 2 H), 2.20 (m, 1 H), 2.38 (m, 1 H), 2.75–3.05 (m, 5 H), 3.20 (dd,1 H), 3.28 (t, 1 H), 3.41 (t, 1 H), 4.43 (m, 1 H), 6.60 (d, 2 H), 6.80 (d, 1 H), 6.97 (q, 2 H), 7.15 (d, 1 H), 7.2–7.4 (m, 4 H), 7.62 ppm (d, 1 H).
M.S.(FAB); m/e 481$(M+H)^+$.

EXAMPLE 10

N-[1-D,L-Carboxy-3-(4-hydroxyphenyl)propyl]-L-histidyl-glycine

The procedure of Example 9 was followed but L-histidyl glycine was substituted for L-histidyl-L-phenylalanine. The residue from the Dowex 50 chromatography was dissolved in 10 ml of 3% (v/v) pyridine in water and the solution concentrated under vaccuum to a 2 ml volume. Methanol was added dropwise to this solution and the solid which formed was collected and dried under vacuum to provide the title compound.

p.m.r.: ($D_2O$) δ:1.72 (m, 2 H), 2.23 (m, 2 H), 2.85–3.08 (pair of q, 2 H), 3.09 (t,1 H), 3.36 (s, 3 H), 3.46 (q, 1 H), 3.75 (q, 1 H), 6.58 (d, 2 H), 6.92 (d, 2 H), 6.99 (s, 1 H), 7.68 ppm (s, 1 H).

EXAMPLE 11

N-[1-D,L-Carboxy-3-(4-hydroxyphenyl)propyl]-L-histidyl-L-glutamic acid, ammonium salt The procedure of Example 9 was followed but L-histidyl-L-glutamic acid was substituted for L-histidyl-L phenylalanine. The residue from the Dowex 50 chromatography was dissolved in $H_2O$ and applied to a 10 ml Dowex AGl (OH-cycle) column. The column was washed with water then with 3% (v/v) acetic acid in water. The second eluate was concentrated under vacuum to provide the title compound as a white solid.
Anal. C,H,N,: Calc. C 48.93; H 6.45; N 13.59
Found C 48.82; H 6.17; N 13.68

EXAMPLE 12

N-[1-D,L-Carboxy-3-(4-hydroxyphenyl)propyl]-L-histidyl-L-methionine Ammonium salt The procedure of Example 9 was followed but L-histidyl-L-methionine was substituted for L-histidyl-L-phenylalanine. The residue from the Dowex 50 chromatography was dissolved in H$_2$O and HPLC chromatography (85 water:15 acetonitrile:0.1 trifluoroacetic acid) provided the title compound as a white solid.

p.m.r.: (D$_2$O) δ:1.98 (m, 1 H), 2.13 (d, 3 H), 2.15–2.60 (m, 4H), 2.65–2.90 (m, 2 H), 3.40–3.60 (m, 2 H), 3.89 (m, 1 H), 4.34 (q, 1 H), 4.53 (m, 1 H), 6.94 (d, 2 H), 7.29 (d, 2 H), 7.50 (d, 1 H), 8.75 ppm (s, 1 H).

EXAMPLE 13

N-[1-D,L-Carboxy-3-(4-hydroxyphenyl)propyl]-L-histidyl-L-tyrosine

The procedure of Example 9 was followed, but L-histidyl-L-tyrosine was substituted for L-histidyl-L-phenylalanine. Dowex 50 chromatography provided the title compound as a solid. Not purified further.

p.m.r.: (D$_2$O) δ: 1.80 (m, 2 H), 2.46 (m, 2 H), 2.80–3.10 (m, 5 H), 3.20 (dd, 1 H), 3.24 (t, 1 H), 3.88 (t, 1 H), 4.40 (m, 1 H), 6.65 (d, 2 H), 6.80 (d, 2 H), 7.04 (q, 2 H), 7.15 (d, 1 H) 7.2–7.3 (m, 4H), 8.40 (s, 1 H), 8.44 ppm (s, 1 H);
M.S. (FAB): m/e 497(M+H)$^+$.
Anal. C,H,N: Calc. C 56.38; H 6.06; N 10.52
Found C 56.78; H 5.70; N 10.12

EXAMPLE 14

N-[1-D,L-Carboxy-3-(4-hydroxyphenyl)propyl]-L-histidyl-L-alanine

A solution of 113 mg of L-histidyl-L-alanine and 486 mg of 4-(4 hydroxyphenyl)-2-oxobutanoic acid in ethanol and water was basified to pH 7.2 with 0.1 N aqueous sodium hydroxide solution. Sodium cyano borohydride (158 mg) was added and the reaction mixture was stirred at ambient temperature for 11 days. Dowex 50W-2X resin was then added and the mixture stirred 0.5 hours. The mixture was then applied to a Dowex 50W resin column and the column washed with water until the eluate was neutral, then with 5% (v/v) ethanol in water and finally with 3% (v/v) pyridime in water. The last eluate was concentrated under vacuum to provide the title compound as a white solid.
M.S.(FAB): m/e 405(M+H)$^+$.

EXAMPLE 15

N-[1-D,L-Carboxy-3-(4-hydroxyphenyl)propyl]-L-histidyl-L-proline sodium salt

Using the procedure of Example 14 but substituting L-histidyl-L-proline for L-histidyl-L-alanine provided the title compound.

p.m.r.: (D$_2$O) δ:1.93 (m, 4 H), 2.24 (m, 1 H), 2.62 (m, 2 H), 3.21–3.40 (m, 4 H), 3.54 (m, 1 H), 4.00 (m, 1 H), 4.30 (m, 1 H), 6.88 (d, 2 H), 7.08 (d, 2 H), 7.10–7.34 (m, 4 H), 8.40 ppm (s, 1 H);
M.S. (FAB) m/e 431 (M+H$^+$), 453 (M+Na)$^+$.
Anal. C,H,N: Calc. C 51.48; H 6.13; N 11.44
Found C 51.27; H 6.16; N 11.55

EXAMPLE 16

N-[1-D,L-Carboxy-3 (4-hydroxyphenyl)propyl]-L-histidyl-L-tryptophane

Using the procedure of Example 14, but substituting L-histidyl-L-tryptophane hydrochloride for L-histidyl-L-alanine provided the title compound.

p.m.r.: (D$_2$O) δ:1.58 (m, 2 H), 2.14 (m, 2 H), 2.80–3.38 (m, 6 H), 4.48 (m, 2 H), 6.60 (t, 2 H), 6.78 (s, 1 H), 6.86 (t, 2 H), 6.90 (m, 4 H), 7.45 (m, 4 H), 8.55 ppm (d, 1 H);
M.S. (FAB): m/e 520(M+H)$^+$.

EXAMPLE 17

N-[1-D,L-Carboxy-3-(4-hydroxyphenyl)propyl]-L-histidyl-L-serine

Using the procedure of Example 14, but substituting L-histidyl-L-serine for L-histidyl-L-alanine provided the title compound.
M.S. (FAB): m/e 421 (M+H)$^+$.

EXAMPLE 18

N-(1-D,L-Carboxy-3-phenylpropyl)-L-histidyl-L-histidine

A solution of 110 mg of L-histidyl-L-histidine and 442 mg of 4-phenyl-2-oxobutanoic acid was dissolved in 3 ml of water and the mixture was adjusted to pH7 by addition of concentrated aqueous sodium hydroxide solution. Sodium cyanoborohydride (50 mg) was added to the solution and the mixture was then stirred at ambient temperature for 16 hours. Dowex 50 resin (7 ml) was added and the mixture stirred 2 hours at ambient temperature. The mixture was then added to a 15 ml Dowex 50 column and the column washed with 50 ml of 1:1 acetonitrile:water and 100 ml of water. The column was then eluted with 3% (v/v) pyridine in water and this eluate concentrated under vacuum to provide 144 mg of the title compound as a white solid.

p.m.r.: (D$_2$O) δ: 1.96 (m, 2 H), 2.66 (m, 2 H), 3.00–3.36 (m, 5 H), 3.72 (t, 1 H), 4.48 (m, 1 H), 7.2–7.45 (m, 8H), 8.35–8.50 ppm (m, 2 H);
M.S. (FAB): m/e 455(M+H)$^+$.

EXAMPLE 19

N-(1-D,L-Carboxy-3-methylbutyl) L-aspartyl-L-tyrosine

A solution of 148 mg of L-aspartyl-L-tyrosine and 380 mg of 4-methyl-2-oxopentanoic acid sodium salt in water and ethanol was adjusted to pH 7 by addition of 0.1 M aqueous sodium hydroxide solution. Sodium cyanoborohydride (252 mg) was added and the reaction mixture stirred seven days at ambient temperature. Dowex 50W-2X resin was then added and the mixture stirred overnight. The mixture was then applied to a Dowex 50W column and the column washed with H$_2$O until the eluent was neutral. The column was then eluted with 300 ml of 3% (v/v) pyridine in water. This eluate was concentrated under vacuum to provide 155.7 mg of the title compound as a white fluffy solid.

p.m.r.: (D$_2$O) δ: 0.80 (d, 2 H), 0.95 (d, 6 H), 1.64 (m, 4 H), 2.95 (m, 4 H), 3.21–3.38 (m, 4 H), 4.18 (m, 2 H), 6.88 (d, 2 H), 7.10 ppm (d, 2 H);
M.S.(FAB): m/e 411 (M+H)$^+$.

EXAMPLE 20

(N$^α$-Carboxymethyl-L-histidyl)-L-leucyl-glycine

Step A: (N$^α$-t-Butoxycarbonyl-L-leucyl)glycine benzyl ester

Using the procedure of Example 5 (step A) but substituting glycine benzyl ester hydrochloride for L-leucine benzyl ester p-tosylate and substituting N$^α$-t-butoxycarbonyl-L-leucine N-hydroxysuccinimide ester for N$^α$-t-butoxycarbonyl-L-aspartic β-benzyl-α-N-hydroxysuccinimide diester provided the title compound.

Step B: (L-Leucyl)glycine benzyl ester

A stirred solution of 1.29 g of the ester from Example 20 (step A) in 3.5 ml of methylene chloride was treated with 3.5 ml of trifluoroacetic acid and the solution stirred 2.5 hours at ambient temperature. The solution was then concentrated under a stream of nitrogen and the residue dissolved in methylene chloride/diethyl ether. The solution was washed 2 times with saturated aqueous sodium carbonate solution and the organic phase was then dried with sodium sulfate and filtered. Concentration under vacuum provided 919 mg of the title compound as a yellow oil.

Step C to Step F:
($N^\alpha$-Carboxymethyl-L-histidyl)-L-leucyl-glycine

The procedure of Example 1 (Step A to Step D), but substituting the benzyl ester of Example 20 (step B) for L-leucine benzyl ester, provided the title compound.

p.m.r.: (DMSO-$d_6$) δ: 0.83 (d,3 H), 0.87 (d,3 H), 1.4–1.6 (m,3 H), 2.76 (dd,1 H), 2.87 (dd,1 H), 3.11 (d,1 H), 3.25 (d,1 H), 3.41 (m,1 H), 3.73 (d,2 H), 4.34 (m,1 H), 6.88 (s,1 H), 7.59 (s,1 H), 8.17 (d,1 H), 8.57 ppm (br. m, 1 H); MS (FAB): m/e 384(M+H)+.

EXAMPLE 21

$N^\alpha$-Carboxymethyl-L-histidine

Step A: $N^\alpha$-t-Butoxycarbonyl $N^{im}$-2,4-dinitrophenyl-L-histidine benzyl ester A mixture of 2.2 g of $N^\alpha$-t-butoxycarbonyl-$N^{im}$-2,4-dinitrophenyl-L-histidine monohydrate, 0.62 ml of benzyl alcohol, 1.03 g of N,N'-dicyclohexylcarbodiimide and 1.53 g of 1-hydroxybenzotriazole in 20 ml of methylene chloride was stirred overnight at ambient temperature. The mixture was then filtered and the solid rinsed with methylene chloride. The filtrates were combined and concentrated under vacuum. Chromatography of the residue over silica gel (gradient 1% to 2% methanol in methylene chloride) provided 1.76 g of the title compound.

Step B to Step D: $N^\alpha$-Carboxymethyl-L-histidine

Using the procedure of Example 1 (steps B to D), but substituting the histidine benzyl ester of Example 21 (step A) for the dipeptide of Example 1 (step A) provided the title compound.

p.m.r.: (D$_2$O) δ: 3.35–3.55 (m,2 H), 3.65, 3.76 (d, each 1 H), 4.05 (m,1 H), 7.46 (s,1 H), 8.69 ppm (s,1 H); MS (FAB) m/e 214(M+H)+.

EXAMPLE 22

N-[1-D,L-Carboxy-3-(4-hydroxyphenyl)propyl]-L-histidyl-β-alanine sodium salt

Using the procedure of Example 6 (step C) but substituting L-histidyl-L-alanine for the dipeptide of Example 6 (step B) provided the title compound.

MS (FAB): m/e 405 (M+H)+.
p.m.r.: (D$_2$O) δ: 1.92 (t,2 H), 2.24 (t,2 H), 2.58 (t,2 H), 3.06 (t,2 H), 3.32 (m,4 H), 6.86 (d,2 H), 7.16 (d,2 H), 8.14 (s,1 H), 8.24 ppm (s,1 H).

EXAMPLE 23

N-[1-D,L-Carboxy-2-(4-hydroxyphenyl)ethyl]-L-histidine

Using the procedure of example 6 (step C), but substituting L-histidine for the dipeptide of Example 6 (step B) and 3-(4-hydroxyphenyl)-2-oxopropanoic acid for 4-(4-hydroxyphenyl)-2-oxobutanoic acid, provided the title compound.

p.m.r.: (D$_2$O) δ: 1.88 (d,2 H), 2.25 (d,2 H), 3.00 (m,1 H), 3.07 (m,1 H), 3.15 (m,1 H), 3.52 (t,1 H), 6.87 (d,2 H), 6.97 (s, 1 H), 7.17 (d,2 H), 7.71 ppm (s,1 H).

EXAMPLE 24

$N^\alpha$-[1-L-Carboxy-2-(3-indolyl)ethyl]-L-histidyl-L-glutamic acid bistrifluoroacetate Using the procedure of Example 9, but substituting L-histidyl-L-glutamic acid for L-histidyl-L-phenylalanine and substituting 3-(3-indolyl)-2-oxopropanoic acid for 4-(4-hydroxyphenyl)-2-oxobutanoic acid, provided a mixture of diastereomeric peptides which were resolved by HPLC chromatography to provide the title compound.

p.m.r.: (D$_2$O) δ: 1.90 (m,1 H), 2.10 (m,1 H), 2.42 (t,2 H), 3.3–3.5 (m,3 H), 3.62 (dd,1 H), 4.12 (t,1 H), 4.19 (m,2 H), 7.20 (s,1 H), 7.30 (t,1 H), 7.39 (m,3 H), 7.57 (s,1 H), 7.64 (d,1 H), 7.77 ppm (d,1 H).

EXAMPLE 25

N-[1-D,L-Carboxy-3-(4-hydroxyphenyl)propyl]-L-histidyl-L-phenylalaninamide

Using the procedure of Example 6, but substituting phenylalaninamide for β-(2-thienyl)-L-alanine, provided the title compound.

p.m.r.: (CD$_3$OD) δ: 1.8–2.0 (m,2 H), 2.4–2.6 (m,2 H), 2.9–3.2 (m,5 H), 3.65–3.8 (m,1 H), 4.65–4.75 (m,1 H), 6.72 (d,2 H), 6.96–7.05 (m,4 H), 7.27 (m,5 H), 7.48 (m,1 H), 7.85–8.05 (m,2 H), 8.55 ppm (dd,1 H).

EXAMPLE 26

($N^\alpha$-Carboxymethyl-L-histidyl)-L-phenylalanine

Using the procedure of Example 1, but substituting L-phenylalanine benzyl ester for L-leucine benzyl ester, provided the title compound as an off-white powder.

p.m.r.: (DMSO-$d_6$) δ: 2.60 (dd,1 H), 2.74 (dd, 1 H), 2.85–3.15 (m,4H), 3.28 (m,1 H), 4.45 (m,1 H), 6.84 (s,1 H), 7.1–7.3 (m,5 H), 7.65 (s,1 H), 8.21 ppm (d,1 H); MS (FAB): m/e 361 (M+H)+.

EXAMPLE 27

($N^\alpha$-Carboxymethyl-L-tryptophyl)-L-leucine

The procedure of Example 1 (steps A,B, and D) was employed but $N^\alpha$-t-butoxycarbonyl-L-tryptophan N-hydroxysuccinimide ester was reacted with L-leucine benzyl ester in the absence of N,N'-dicyclohexyl-carbodiimide and 1-hydroxybenzotriazole in step A. This provided the title compound as an off white powder.

p.m.r.: (DMSO-$d_6$) δ: 0.80 (d,3 H), 0.86 (d,3 H), 1.49 (m,3 H), 2.91 (dd,1 H), 3.07 (d superimposed on m,2 H), 3.25 (d,1 H), 3.49 (m,1 H), 4.23 (m,1 H), 6.87 (t,1 H), 7.06 (t,1 H), 7.20 (s,1 H), 7.33 (d,1 H), 7.55 (d,1 H), 8.14 ppm (d,1 H); MS (FAB): m/e 376 (M+H)+.

EXAMPLE 28

($N^\alpha$-Carboxymethyl-L-histidyl)-L-aspartic acid

Using the procedure of Example 1, but substituting L-aspartic acid dibenzyl ester for L-leucine benzyl ester provided the title compound as a white powder.

p.m.r.: (DMSO-$d_6$) δ: 2.54 (dd,1 H), 2.67 (dd,1 H), 2.76 (dd,1 H), 2.89 (dd,1 H), 3.13 (d,1 H), 3.31 (d,1 H), 3.39 (m,1 H), 4.44 (m,1 H), 7.02 (s,1 H), 7.92 (s,1 H), 8.28 ppm (d,1 H); MS (FAB): m/e 326 (M+H)+.

EXAMPLE 29

N$^\alpha$-Carboxymethyl-L-histidyl)-L-leucinamide

Using the procedure of Example 1, but substituting L-leucinamide for L-leucine benzyl ester, provided the title compound as a white solid.

p.m.r.: (DMSO-d$_6$) δ: 0.83 (d,3 H), 0.86 (d,3 H), 1.47 (m,3 H), 2.6–3.5 (m,5 H), 4.24 (m,1 H), 6.83 (s,1 H), 7.52 ppm (s,1 H); MS (FAB): m/e 326 (M+H)$^+$.

EXAMPLE 30

N$^\alpha$-Carboxymethyl-L-aspartyl)-glycine

Using the procedure of Example 5, but substituting glycine benzyl ester for L-leucine benzyl ester, provided the title compound as a white solid.

p.m.r.: (DMgO-d$_6$) δ: 3.1–3.6 (m,6 H), 3.76 (m,1 H), 8.36 ppm (m,1 H); MS (FAB): m/e 249 (M+H)$^+$.

EXAMPLE 31

N$^\alpha$-Carboxymethyl-D-histidyl)-L-leucine

Using the procedure of Example 3, but substituting N$^\alpha$-t-butoxycarbonyl-N$^{im}$-2,4-dinitrophenyl-D-histidine for the corresponding protected L-histidine, provided the title compound as a white solid.

p.m.r.: (DMSO-d$_6$) δ: 0.83 (d,3 H), 0.88 (d,3 H), 1.52 (m,3 H), 2.73 (dd,1 H), 2.86 (dd,1 H), 3.11 (d,1 H), 3.28 (d,1 H), 3.39 (m,1 H), 4.23 (m,1 H), 6.89 (s,1 H), 7.64 (s,1 H), 8.18 ppm (d,1 H); MS (FAB): m/e 327 (M+H)$^+$.

EXAMPLE 32

(N$^\alpha$-Carboxymethyl-D-histidyl)glycine

Using the procedure of Example 4, but substituting N$^\alpha$-t-butoxycarbonyl-N$^{im}$-(2,4-di-nitrophenyl)-D-histidine for the protected L-histidine, provided the title compound as a white solid. p.m.r.: (DMSO-d$_6$) δ: 2.73 (dd,1 H), 2.88 (dd,1 H), 3.12 (d,1 H), 3.31 (d,1 H), 3.38 (m, 1 H), 3.74 (m,1 H), 6.92 (s,1 H), 7.68 (s,1 H), 8.32 ppm (m,1 H); MS (FAB): m/e 271 (M+H)$^+$.

EXAMPLE 33

(N$^\alpha$-Carboxymethyl-L-histidyl)cycloleucine

Using the procedure of Example 1, but substituting cycloleucine benzyl ester [P. Tailleur and L. Berlinguet, Can. J. Chem., 39, 1309 (1961)] for L-leucine benzyl ester, provided the title compound as a white solid.

p.m.r.: (DMSO-d$_6$) δ: 1.59 (m,4 H), 1.83 (m,2 H), 2.02 (m,2 H), 2.73 (dd,1 H), 2.81 (dd,1 H), 3.10 (d,1 H), 3.22 (d,1 H), 3.40 (t,1 H), 6.88 (s,1 H), 7.63 (s,1 H), 8.23 ppm (s,1 H); MS (FAB): m/e 325 (M+H)$^+$.

EXAMPLE 34

(N$^\alpha$-Carboxymethyl-L-histidine methyl ester

The procedure of Example 1 (Step B, C, D) was employed, but N$^{im}$-(2,4-dinitrophenyl)-L-histidine methyl ester was substituted for the in situ generated N$^{im}$-(2,4-dinitrophenyl)-L-histidyl-L-leucine dibenzyl ester in Step B (reaction with benzyl bromoacetate).

The product from that step was then employed in the procedure of Example 1 (steps C and D) to provide the title compound as a white solid.

p.m.r.: (DMSO-d$_6$) δ: 2.88 (m,2 H), 3.1–3.4 (m,3 H), 3.60 (s,3 H), 6.78 (s,1 H), 7.53 ppm (s,1 H); MS (FAB): m/e 228 (M+H)$^+$.

What is claimed is:

1. A method of inhibiting herpes simplex virus ribonucleotide reductase which comprises exposing said ribonucleotide reductase to an inhibitorally effective amount of a peptide of formula:

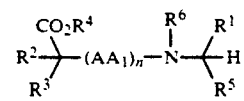

wherein:

AA$_1$ is histidine, aspartic acid or any of the enantiomorphic forms thereof;

R$^1$ is:
- a) hydrogen;
- b) C$_2$–C$_6$ alkenyl;
- c) C$_2$–C$_6$ alkynyl;
- d) C$_3$–C$_7$ cycloalkyl;
- e) C$_5$–C$_7$ cycloalkenyl;
- f) phenyl;
- g) monocyclic heteroaromatic ring system;
- h) aromatic polycyclic or heteroaromatic polycyclic ring system;
- i) C$_1$–C$_6$ alkyl;
- j) a group f)-i), above, monosubstituted by: OH, OCH$_3$, NH$_2$, SCH$_3$, C$_{1-4}$ alkyl, CO$_2$H or CN;
- k) C$_1$–C$_4$ alkyl monosubstituted by b)-j) hereinabove;

R$^2$ and R$^3$ are independently:
- l) hydrogen;
- m) C$_2$–C$_6$ alkenyl;
- n) C$_2$–C$_6$ alkynyl;
- o) C$_3$–C$_7$ cycloalkyl;
- p) C$_5$–C$_7$ cycloalkenyl;
- q) phenyl;
- r) monocyclic heteroaromatic ring system;
- s) aromatic polycyclic or heteroaromatic polycyclic ring system;
- t) C$_2$–C$_6$ alkyl
- u) a group q)-t), above, monosubstituted by: OH, OCH$_3$, NH$_2$, SCH$_3$, C$_{1-4}$ alkyl, CO$_2$H, or CN;
- v) C$_1$–C$_4$ alkyl monosubstituted by m)-u) hereinabove;
- w) R$^2$ and R$^3$ combined to form a C$_3$–C$_5$ diradical;

R$^4$ is: H, C$_3$–C$_7$ cycloalkyl, or C$_1$–C$_6$ alkyl;

R$^5$ is: CO$_2$R$^4$, CH$_2$CO$_2$R$^4$, PO$_3$R$^4$, CONHCH$_2$CO$_2$R$^4$ or CONH$_2$;

R$^6$ is: H, CH$_3$ or R$^1$ and R$^6$ are combined to form a C$_2$–C$_4$ diradical;

n is 1.

2. The method of claim 1 wherein the peptide employed is:

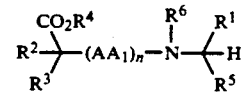

AA$_1$ is histidine or the enantiomorphic form thereof;

R$^1$ is:
- x) hydrogen;
- y) C$_1$–C$_6$ alkyl;
- z) phenyl;
- aa) a group y) or z) monosubstituted by: OH, OCH$_3$, NH$_2$, SCH$_3$, C$_1$–C$_4$ alkyl, CO$_2$H or CN;
- bb) C$_1$–C$_4$ alkyl monosubstituted by y)-aa) hereinabove;

R$^2$ and R$^3$ are independently:
- cc) hydrogen;

dd) phenyl;
ee) monocyclic heteroaromatic ring system;
ff) aromatic polycyclic or heteroaromatic polycyclic ring system;
gg) $C_1-C_6$ alkyl;
hh) a group dd)-gg) above, monosubstituted by: OH, OCH$_3$, NH$_2$, SCH$_3$, $C_{1-4}$ alkyl, CO$_2$H or CN;
ii) $C_1-C_4$ alkyl monosubstituted by dd)-hh) above;
R$^4$ is hydrogen or methyl, R$^5$ is CO$_2$H or PO$_3$H and R$^6$ is hydrogen, methyl or R$^6$ and R$^1$ are combined to form a $C_2-C_4$ alkyl diradical; and
n is 1.

3. The method of claim 2 wherein the peptide employed is:

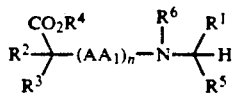

wherein:
AA$_1$ is L-histidine;
R$^1$ is:
jj) hydrogen;
kk) $C_1-C_6$ alkyl;
ll) a group kk) monosubstituted by: OH, OCH$_3$, NH$_2$, SCH$_3$, $C_1-C_4$
R$^2$ is:
mm) hydrogen;
nn) phenyl;
oo) a group nn) monosubstituted by: OH, OCH$_3$, NH$_2$, SCH$_3$, $C_1-C_4$ alkyl, CO$_2$H or CN;
pp) $C_1-C_4$ alkyl monosubstituted by nn) or oo) hereinabove;
R$^3$ is hydrogen;
R$^4$ and R$^6$ are independently hydrogen or methyl or R$^1$ and R$^6$ are combined to form a $C_2-C_4$ diradical;
R$^5$ is CO$_2$H or PO$_3$H; and
n is 1.

4. A method of inhibiting herpes simplex virus ribonucleotide reductase which comprises exposing said ribonucleotide reductase to an inhibitorally effective ammount of a peptide, where the peptide employed is selected from:
(N$^\alpha$carboxymethyl-L-histidyl)-L-leucine;
(N$^\alpha$carboxymethyl-D-histidyl)-L-leucine;
(N$^\alpha$carboxymethyl-L-histidyl)-D-leucine;
(N$^\alpha$carboxymethyl-L-histidyl)glycine;
(N$^\alpha$carboxymethyl-L-aspartyl)-L-leucine;
N-[1-D,L-carboxy-3-(4-hydroxyphenyl)propyl]-L-histidyl-$\beta$-(2-thienyl)-L-alanine;
N-[1-D,L-carboxy-3-(4-hydroxyphenyl)propyl]-L-histidyl-L-homophenylalanine;
N-[1-D,L-carboxy-3-(4-hydroxyphenyl)propyl]-$\beta$-(4-thiazolyl)-L-alanyl-glycine;
N-[1-D,L-carboxy-3-(4-hydroxyphenyl)propyl]-L-histidyl-L-phenylalanine hemiammonium, hemisodium salt;
N-[1-D,L-carboxy-3-(4-hydroxyphenyl)propyl]-L-histidyl-glycine;
N-[1-D,L-carboxy-3-(4-hydroxyphenyl)propyl]-L-histidyl-L-glutamic acid, ammonium salt;
N-[1-D,L-carboxy-3-(4-hydroxyphenyl)propyl]-L-histidyl-L-methionine ammonium salt;
N-[1-D,L-carboxy-3-(4-hydroxyphenyl)propyl]-L-histidyl-L-tyrosine;
N-[1-D,L-carboxy-3-(4-hydroxyphenyl)propyl]-L-histidyl-L-alanine;
N-[1-D,L-carboxy-3-(4-hydroxyphenyl)propyl]-L-histidyl-L-proline sodium salt;
N-[1-D,L-carboxy-3-(4-hydroxyphenyl)propyl]-L-histidyl-L-tryptophane;
N-[1-D,L-carboxy-3-(4-hydroxyphenyl)propyl]-L-histidyl-L-serine;
N-(1-D,L-carboxy-3-phenylpropyl)-L-histidyl-L-histidine;
N-(1-D,L-carboxy-3-methylbutyl)-L-aspartyl-L-tyrosine;  (N$^\alpha$-carboxymethyl-L-histidyl)-L-leucyl-glycine;
N-[1-D,L-carboxy-3-(4-hydroxyphenyl)propyl]-L-histidyl-$\beta$-alanine sodium salt;
N-[1-D,L-carboxy-3-(4-hydroxyphenyl)propyl]-L-histidyl-L-phenylalaninamide;
N$^\alpha$-[1-L-carboxy-2-(3-indolyl)ethyl]-L-histidyl-L-glutamic acid bistrifluoroacetate;
(N$^\alpha$-carboxymethyl-L-histidyl)-L-phenylalanine;
(N$^\alpha$-carboxymethyl-L-tryptophyl)-L-leucine;
(N$^\alpha$-carboxymethyl-L-histidyl)-L-aspartic acid;
(N$^\alpha$-carboxymethyl-L-histidyl)-L-leucinamide;
(N$^\alpha$-carboxymethyl-L-aspartyl)-glycine;
(N$^\alpha$-carboxymethyl-D-histidyl)-D-leucine;
(N$^\alpha$-carboxymethyl-D-histidyl)glycine;
(N$^\alpha$-carboxymethyl-L-histidyl)cycloleucine; and
(N$^\alpha$-carboxymethyl-L-histidine methyl ester.

* * * * *